United States Patent [19]

Kohn et al.

[11] Patent Number: 4,499,271

[45] Date of Patent: Feb. 12, 1985

[54] 3-PHOSPHINYLOXY-4-(SUBSTITUTED PHENOXY)ALKENOIC ACID ESTERS

[75] Inventors: Gustave K. Kohn, Palo Alto; Joe T. Bamberg, Redwood City, both of Calif.

[73] Assignee: Zoecon Corporation, Palo Alto, Calif.

[21] Appl. No.: 410,173

[22] Filed: Aug. 20, 1982

[51] Int. Cl.³ ............................................. C07F 9/58
[52] U.S. Cl. ................................... 546/22; 260/934; 546/23; 544/354; 548/113; 71/94
[58] Field of Search ........................................ 546/22

[56] References Cited

U.S. PATENT DOCUMENTS

| 3,379,752 | 4/1968 | Bolhofer ............................... 560/53 |
| 4,216,007 | 8/1980 | Nishiyama et al. ..................... 71/94 |
| 4,322,375 | 4/1982 | Maier .................................. 260/951 |

FOREIGN PATENT DOCUMENTS

| 0050019 | 4/1982 | European Pat. Off. ............ 546/302 |
| 57-48990 | 3/1982 | Japan .................................... 546/22 |

*Primary Examiner*—Alan L. Rotman
*Attorney, Agent, or Firm*—Jacqueline S. Larson; Hana Dolezalova

[57] ABSTRACT

3-Phosphinyloxy-4-substituted phenoxy alkenoic acid esters, derivatives thereof, and the use thereof for the control of weeds.

7 Claims, No Drawings

3-PHOSPHINYLOXY-4-(SUBSTITUTED PHENOXY)ALKENOIC ACID ESTERS

This invention relates to novel 3-phosphinyloxy-4-substituted phenoxy alkenoic acid esters, derivatives thereof, and the use thereof for the control of weeds.

More particularly, the compounds of the present invention are represented by the following formula (A):

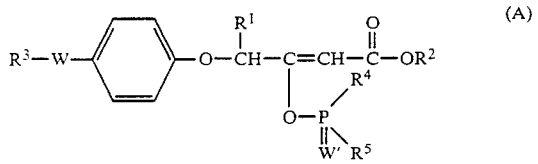

wherein,
$R^1$ is hydrogen or lower alkyl;
$R^2$ is lower alkyl, lower alkenyl or lower alkynyl;
W is oxygen, sulfur or amino;
W' is oxygen or sulfur;
$R^3$ is one of the groups

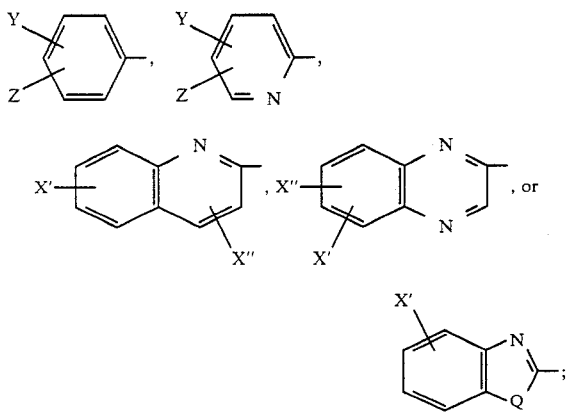

in which,
each of Y and Z is independently selected from hydrogen, lower alkyl, lower haloalkyl, lower alkoxy, lower haloalkoxy, bromo, chloro, fluoro, nitro and cyano;
each of X' and X" is independently selected from hydrogen, fluoro, chloro, bromo, trifluoromethyl, methoxy or nitro, provided that both X' and X" cannot be trifluoromethyl, methoxy or nitro; and
Q is oxygen or sulfur;
$R^4$ is lower alkyl, lower haloalkyl, lower cycloalkyl, substituted or unsubstituted aryl, substituted or unsubstituted aralkyl, —$OR^6$, —$SR^6$ or —$NHR^6$;
$R^5$ is lower alkyl, lower haloalkyl, lower cycloalkyl, substituted or unsubstituted aryl, substituted or unsubstituted aralkyl, —$OR^7$, —$SR^7$ or —$NHR^7$;
$R^6$ is lower alkyl, lower haloalkyl, substituted or unsubstituted aryl, or substituted or unsubstituted aralkyl; and
$R^7$ is independently selected from the values of $R^6$.

In the description and claims hereinafter, each of $R^1$-$R^7$, Q, W, W', X', X", Y and Z is as defined above, unless otherwise specified.

The compounds of formula (A) can be synthesized by treatment of a 3-oxocarboxylate of formula (I) with NaH and reaction of the resulting corresponding sodium salt with a halide of formula (II), following the procedure of Sum and Weiler, *Tetrahedron (Supp.* 9) 37:303–318, at p. 311.

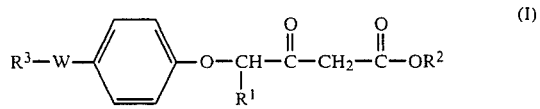

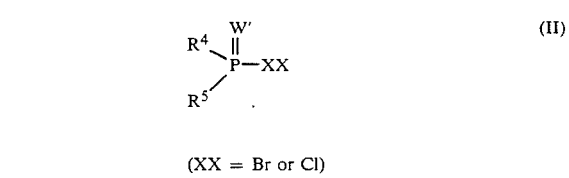

(XX = Br or Cl)

Alternatively, the compounds of (A) where $R^4$ is —$OR^6$, —$SR^6$ or —$NHR^6$ and $R^5$ is —$OR^7$, —$SR^7$ or —$NHR^7$ can be prepared as described by Leber et al., German Offenlegungschrifft No. 1,940,003 (CA 72:89801u, 1970), by reacting a 3-oxocarboxylate of formula (I) with phosphoryl chloride or thiophosphoryl chloride in the presence of triethylamine or sodium hydroxide to give the intermediate (III), which is reacted with one equivalent of each of $R^6OH$ and $R^7OH$, or of $R^6SH$ and $R^7SH$, or of $R^6NH_2$ and $R^7NH_2$.

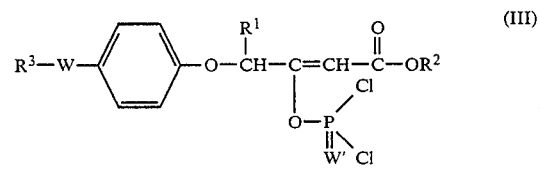

3-oxocarboxylates of formula (I) can be prepared as described by S. Lee U.S. Pat. No. 4,408,076, the entire disclosure of which is incorporated herein by reference.

One embodiment of the present invention is represented by formula (B) below:

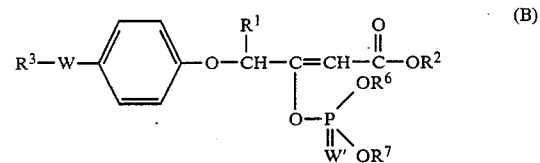

Another embodiment of the present invention is represented by formula (C) below:

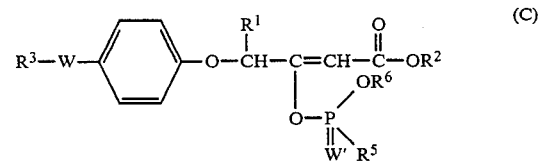

wherein $R^5$ is other than —$OR^7$, —$SR^7$ or —$NHR^7$.

The following terms, wherever used in the description herein and in the appended claims, have the meaning defined below, unless the otherwise specified hereinafter.

The term "lower alkyl" refers to an alkyl group, straight or branched, having a chain length of one to eight carbon atoms. The term "lower haloalkyl" refers to a lower alkyl group substituted with one to three halogen atoms.

The term "lower alkoxy" refers to an alkoxy group, straight or branched, having a chain length of one to eight carbon atoms. The term "lower haloalkoxy" refers to a lower alkoxy group substituted with one to three halogen atoms.

The term "lower cycloalkyl" refers to a cycloalkyl group of three to eight cyclic carbon atoms.

The term "aryl" refers to the aryl group phenyl or naphthyl.

The term "aralkyl" refers to a lower alkyl group substituted with an aryl group.

The terms "substituted aryl" and "substituted aralkyl" refer to an aryl group and an aralkyl group, respectively, substituted at one, two or three of the ring carbon atoms with a group selected from lower alkyl, lower haloalkyl, lower alkoxy, lower haloalkoxy, halogen, nitro and cyano.

The novel compounds of formula (A) are useful for the control of weeds, using pre- and/or post-emergent treatments. The compounds can be applied in the form of dusts, granules, solutions, emulsions, wettable powders, flowables and suspensions. Application of a compound of the present invention is made according to conventional procedure to the weeds or their locus using an herbicidally effective amount of the compounds, usually from about one-half or less to ten pounds per acre.

While some of the compounds of the present invention have activity on broad leaf plants, the compounds, in general, demonstrate a higher level of herbicidal activity on the grass weeds. Grass plant (weed) species on which the compounds of the present invention show effective herbicidal activity include shattercane, crabgrass, sprangletop, wild oats, bermudagrass, tall fescue, rice, wheat, barley, corn, blue panicum, foxtails, rough bluegrass, winter rye, annual ryegrass, watergrass and Johnsongrass. It appears to be most effective to apply the active compound prior to the heading stage of the grass weed.

Methods of preparing herbicidal formulations which can be used with a compound of the present invention are described in the literature along with suitable liquid and solid carriers, such as in U.S. Pat. No. 4,192,669 and 4,163,661, which are incorporated herein by reference. The optimum usage of a compound of the present invention is readily determinable by one of ordinary skill in the art using routine testing such as greenhouse testing and small plot testing.

The compounds of the present invention, in view of their broadspectrum grass weed herbicidal activity, can be advantageously combined with broadleaf weed herbicides for broadspectrum postemergence weed control in most broadleaf crops. Examples of herbicides which can be combined with a compound of the present invention include glyphosate, bentazone, diuron, paraquat, 2,4-D, 2,4-DB, diquat, endothal, dinoseb, dicamba, norflurazon, nitrofen, cyanozine, methazole, mefluidide, metribuzin, cycloate, fluometuron, linuron, dalapon, bifenox and alachlor for controlling a broad spectrum of weeds.

The term "herbicide," as used herein, refers to an active ingredient which modifies the growth of plants because of phytotoxic or plant growth regulating properties so as to retard the growth of the plant or damage the plant sufficiently to kill it.

The following examples are provided to illustrate the practice of the present invention. Temperature is given in degrees Centigrade. "RT" means room temperature.

EXAMPLE 1

To NaH (50% in mineral oil, 0.16 g, 3.3 mmol), rinsed with absolute ether (3X, rinses discarded), in ether (5 ml) is added, under $N_2$ with stirring and ice bath, ethyl 4-[4-(4-trifluoromethylphenoxy)phenoxy]-3-oxopentanoate (1.19 g, 3.0 mmol) in ether (5 ml) over several minutes. The mixture is allowed to warm to RT and is stirred at RT for 30 minutes. To this is added diethyl phosphoric chloride (0.52 ml, 3.6 mmol) and stirring is continued overnight. Solid ammonium chloride is then added to the mixture and the mixture is stirred for 30 minutes. Celite is added and the mixture is filtered. The filtrate is diluted with chloroform and is purified by preparative thin layer chromatography (prep. TLC; silica gel developing with 1:4 ethyl acetate/hexane) to give ethyl 4-[4-(4-trifluoromethylphenoxy)phenoxy]-3-diethoxyphosphinyloxy-2-pentenoate (ethyl 4-[4-(4-trifluoromethylphenoxy)phenoxy]-3-diethylphosphoryloxy-2-pentenoate) (cpd. 1 in Table A).

EXAMPLE 2

Following the procedure of Example 1, each of the 3-oxocarboxylates under column I is reacted with NaH and then with diethyl phosphoric chloride to give the corresponding phosphinyloxy compound in Table A.

I 2. ethyl 4-[4-(2-chloro-4-trifluoromethylphenoxy)phenoxy]-3-oxopentanoate.
3. ethyl 4-[4-(2,4-dichlorophenoxy)phenoxy]-3-oxopentanoate.
4. ethyl 4-[4-(4-trifluoromethylphenoxy)phenoxy]-3-oxobutanoate.
5. methyl 4-[4-(4-trifluoromethylphenoxy)phenoxy]-3-oxopentanoate.

EXAMPLE 3

Following the procedure of Example 1, the sodium salt of ethyl 4-[4-(4-trifluoromethylphenoxy)phenoxy]-3-oxopentanoate is reacted with each of the chlorides under column II to give the corresponding compound in Table A.

II 6. dimethyl phosphoric chloride.
7. methyl ethyl phosphoric chloride.
8. S,S'-diethyl dithiophosphoric chloride.
9. methyl ethylphosphonochloridate.
10. methyl phenylphosphonochloridate.
11. O,O'-diethyl thiophosphoric chloride.

TABLE A $$Z\text{-}\underset{Y}{\bigcirc}\text{-}W\text{-}\bigcirc\text{-}O\text{-}CH\text{-}\underset{R^1}{C}=CH\text{-}\underset{|}{\overset{O}{C}}\text{-}OR^2 \quad (V)$$
$$\underset{W'}{\overset{|}{O}}\text{-}P\underset{R^5}{\overset{R^4}{\diagup}}$$

| Cpd | Z | Y | W | $R^1$ | $R^2$ | W' | $R^4$ | $R^5$ |
|---|---|---|---|---|---|---|---|---|
| 1 | $CF_3$ | H | O | $CH_3$ | $CH_2CH_3$ | O | $OCH_2CH_3$ | $OCH_2CH_3$ |
| 2 | $CF_3$ | Cl | O | $CH_3$ | $CH_2CH_3$ | O | $OCH_2CH_3$ | $OCH_2CH_3$ |
| 3 | Cl | Cl | O | $CH_3$ | $CH_2CH_3$ | O | $OCH_2CH_3$ | $OCH_2CH_3$ |
| 4 | $CF_3$ | H | O | H | $CH_2CH_3$ | O | $OCH_2CH_3$ | $OCH_2CH_3$ |

TABLE A-continued $$\text{(V)} \quad \underset{Z}{\overset{Y}{\bigcirc}}-W-\bigcirc-O-CH-\underset{R^4}{\overset{R^1}{C}}=CH-\underset{\underset{W'}{\overset{\|}{O-P}}}{\overset{O}{C}}-OR^2$$

| Cpd | Z   | Y | W | $R^1$ | $R^2$    | W' | $R^4$    | $R^5$    |
|-----|-----|---|---|-------|----------|----|----------|----------|
| 5   | CF₃ | H | O | CH₃   | CH₃      | O  | OCH₂CH₃  | OCH₂CH₃  |
| 6   | CF₃ | H | O | CH₃   | CH₂CH₃   | O  | OCH₃     | OCH₃     |
| 7   | CF₃ | H | O | CH₃   | CH₂CH₃   | O  | OCH₃     | OCH₂CH₃  |
| 8   | CF₃ | H | O | CH₃   | CH₂CH₃   | O  | SCH₂CH₃  | SCH₂CH₃  |
| 9   | CF₃ | H | O | CH₃   | CH₂CH₃   | O  | OCH₃     | CH₂CH₃   |
| 10  | CF₃ | H | O | CH₃   | CH₂CH₃   | O  | OCH₃     | C₆H₅     |
| 11  | CF₃ | H | O | CH₃   | CH₂CH₃   | S  | OCH₂CH₃  | OCH₂CH₃  |

EXAMPLE 4

Following the procedure of Example 1, each of the 3-oxocarboxylates under column III is reacted with NaH and then with diethyl phosphoric chloride to give the corresponding phosphinyloxy compound in Table B.

III 12. ethyl 4-[4-(5-trifluoromethyl-2-pyridyloxy)phenoxy]-3-oxopentanoate.
13. ethyl 4-[4-(3-chloro-5-trifluoromethyl-2-pyridyloxy)phenoxy]-3-oxopentanoate.
14. ethyl 4-[4-(6-fluoro-2-quinolyloxy)phenoxy]-3-pentanoate.
15. ethyl 4-[4-(6-chloro-2-quinoxalinyloxy)phenoxy]-3-pentanoate.
16. ethyl 4-[4-(benzo-1,3-oxazolyl-2-oxy)phenoxy]-3-pentanoate.

TABLE B $$\text{(VI)} \quad R^3-O-\bigcirc-O-\underset{\underset{O}{\overset{\|}{O-P}}\underset{O}{\overset{OCH_2CH_3}{\diagdown}}}{\overset{CH_3}{CH}}-C=CH-\overset{O}{\overset{\|}{C}}-O-CH_2-CH_3$$

| Cpd | $R^3$ |
|-----|-------|
| 12  | F₃C—(pyridyl) |
| 13  | F₃C—(3-chloropyridyl) |
| 14  | 6-fluoroquinolyl |
| 15  | 6-chloroquinoxalinyl |

TABLE B-continued $$\text{(VI)} \quad R^3-O-\bigcirc-O-\underset{\underset{O}{\overset{\|}{O-P}}\underset{O}{\overset{OCH_2CH_3}{\diagdown}}}{\overset{CH_3}{CH}}-C=CH-\overset{O}{\overset{\|}{C}}-O-CH_2-CH_3$$

| Cpd | $R^3$ |
|-----|-------|
| 16  | benzoxazol-2-yl |

EXAMPLE 5

Phosphoryl chloride (7.7 g, 50.0 mmol) in benzene (25 ml) is added within 10 minutes to a mixture of ethyl 4-[4-(4-trifluoromethylphenoxy)phenoxy]-3-oxopentanoate (50.0 mmol) and triethylamine (5.1 g) at −10°, and the resulting mixture is stirred at 0° for 30 minutes and then at 30° for 30 minutes. Methanol (100.0 mmol, 2 equiv.) and triethylamine (10.2 g) are added within 15 minutes at −5°. The reaction mixture is worked up to give ethyl 4-[4-(4-trifluoromethylphenoxy)phenoxy]-3-dimethoxphosphinyloxy-2-pentenoate (cpd. 6, Table A).

In the same manner, ethyl 4-[4-(4-trifluoromethylphenoxy)phenoxy]-3-oxopentanoate is reacted with phosphoryl chloride and then with methanol (1 equiv.) and ethanol (1 equiv.) to give ethyl 4-[4-(4-trifluoromethylphenoxy)phenoxy]-3-methoxyethoxyphosphinyloxy-2-pentenoate (cpd. 7, Table A).

What is claimed is:

1. A compound of the following formula (A):

$$\text{(A)} \quad R^3-W-\bigcirc-O-\underset{\underset{W'}{\overset{\|}{O-P}}\underset{R^5}{\overset{R^4}{\diagdown}}}{\overset{R^1}{CH}}-C=CH-\overset{O}{\overset{\|}{C}}-OR^2$$

wherein,
$R^1$ is hydrogen or lower alkyl;
$R^2$ is lower alkyl, lower alkenyl or lower alkynyl;
W is oxygen, sulfur or amino;
W' is oxygen;
$R^3$ is the group $$\underset{Z}{\overset{Y}{\bigcirc}}_N$$

in which,
  each of Y and Z is independently hydrogen, lower alkyl, lower haloalkyl, bromo, chloro or fluoro;
$R^4$ is —OR⁶, —SR⁶ or —NHR⁶;
$R^5$ is lower alkyl; lower haloalkyl; lower cycloalkyl; phenyl; phenyl substituted with lower alkyl, lower haloalkyl or halogen; benzyl; benzyl substituted with lower alkyl, lower haloalkyl or halogen; —OR⁷; —SR⁷; or —NHR⁷;

$R^6$ is lower alkyl; lower haloalkyl; phenyl; phenyl substituted with lower alkyl, lower haloalkyl or halogen; benzyl; or benzyl substituted with lower alkyl, lower haloalkyl or halogen; and $R^7$ is independently selected from the values of $R^6$.

2. A compound of the following formula (B), according to claim 1:

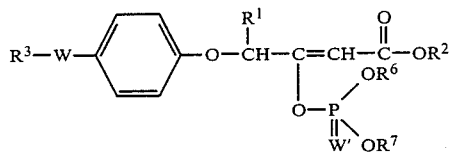 (B)

3. A compound according to claim 2 wherein each of W and W' is oxygen, $R^1$ is methyl, $R^2$ is methyl or ethyl and $R^3$ is

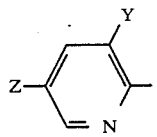

where Y is hydrogen or chloro and Z is chloro or trifluoromethyl.

4. A compound according to claim 3 wherein $R^6$ is methyl or ethyl and $R^7$ is methyl, ethyl or phenyl.

5. A compound of the following formula (C), according to claim 1:

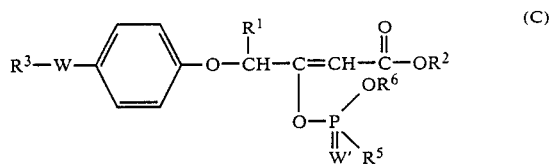 (C)

wherein $R^5$ is other than $-OR^7$, $-SR^7$ or $-NHR^7$.

6. A compound according to claim 5 wherein each of W and W' is oxygen, $R^1$ is methyl, $R^2$ is methyl or ethyl and $R^3$ is

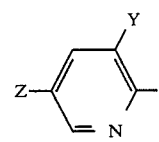

where Y is hydrogen or chloro and Z is chloro or trifluoromethyl.

7. A compound according to claim 6 wherein $R^5$ is methyl, ethyl or phenyl and $R^6$ is methyl or ethyl.

* * * * *